United States Patent [19]

Nasu et al.

[11] Patent Number: 5,246,866
[45] Date of Patent: Sep. 21, 1993

[54] METHOD FOR TRANSCRIPTION OF A DNA SEQUENCE

[75] Inventors: Hisanori Nasu; Toshitsugu Okayama; Hitoshi Fujimiya, all of Yokohama, Japan

[73] Assignee: Hitachi Software Engineering Co., Ltd., Kanagawa, Japan

[21] Appl. No.: 849,631

[22] Filed: Mar. 2, 1992

Related U.S. Application Data

[63] Continuation of Ser. No. 287,113, Dec. 21, 1988, abandoned.

[30] Foreign Application Priority Data

Dec. 23, 1987 [JP] Japan .................. 62-325779
Oct. 7, 1988 [JP] Japan .................. 63-251990

[51] Int. Cl.$^5$ .......................................... G01N 33/00
[52] U.S. Cl. .................................. 436/94; 436/172; 435/6; 250/461.2; 250/580; 204/299 R; 204/182.8; 346/33 A; 346/33 B; 346/33 ME; 935/77; 935/78
[58] Field of Search ............... 436/94, 172; 435/6, 435/291, 301; 250/458.1, 461.1, 461.2, 327.2; 935/77, 78, 86, 87; 346/33 A, 33 B, 33 ME; 204/299 R, 182.8

[56] References Cited

U.S. PATENT DOCUMENTS

| | | | |
|---|---|---|---|
| 2,932,549 | 4/1960 | Kling et al. | 346/33 ME |
| 3,303,508 | 2/1967 | Jaffe et al. | 346/33 ME |
| 3,335,716 | 8/1967 | Alt et al. | 346/33 ME |
| 4,130,824 | 12/1978 | Amos et al. | 346/33 B X |
| 4,706,192 | 11/1987 | Nasu et al. | 364/413 |
| 4,832,815 | 5/1989 | Kambara et al. | 204/182.8 X |
| 4,874,492 | 10/1989 | Mackay | 204/182.8 |
| 4,962,045 | 10/1990 | Picozza et al. | 436/94 X |
| 4,971,677 | 11/1990 | Kambara et al. | 435/6 X |

OTHER PUBLICATIONS

Prober et al, Science, vol. 238, pp. 336–341, Oct. 16, 1987.
Smith et al, Nature, vol. 321, pp. 674–679, Jun. 1986.
Sutherland et al, Anal. Biochem., vol. 163, No. 2, pp. 446–457, Jun. 1987.
Freeman et al. Anal. Biochem., vol. 158, No. 1, pp. 119–129, 1986.

Primary Examiner—James C. Housel
Assistant Examiner—Maureen M. Wallenhorst
Attorney, Agent, or Firm—Fay, Sharpe, Beall, Fagan, Minnich & McKee

[57] ABSTRACT

A DNA sequence transcribing method involves labeling a DNA fragment with a fluorescent substance, subjecting the labeled fragments to electrophoresis, exposing a gel containing the DNA fragment to light during electrophoresis, and detecting fluorescence generated upon exposure. An image corresponding to a fluorescent image on the gel is transcribed on a recording medium by entering a detecting signal in synchronization with operation of detecting fluorescence on the gel containing the DNA fragment after electrophoresis. This arrangement enables a crude fluorescent image on the gel containing the DNA fragment to be recorded as an intact image of the DNA sequencing on the basis of the fluorescent method, and the image can be retained.

1 Claim, 6 Drawing Sheets

FIG. 7
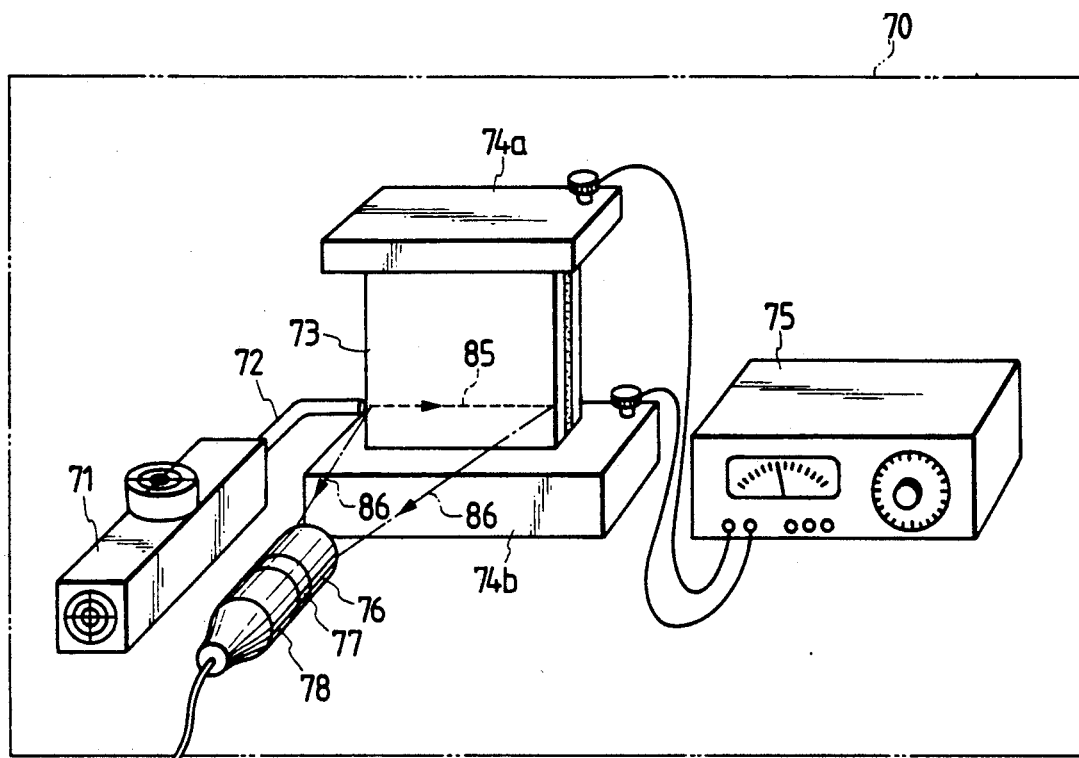
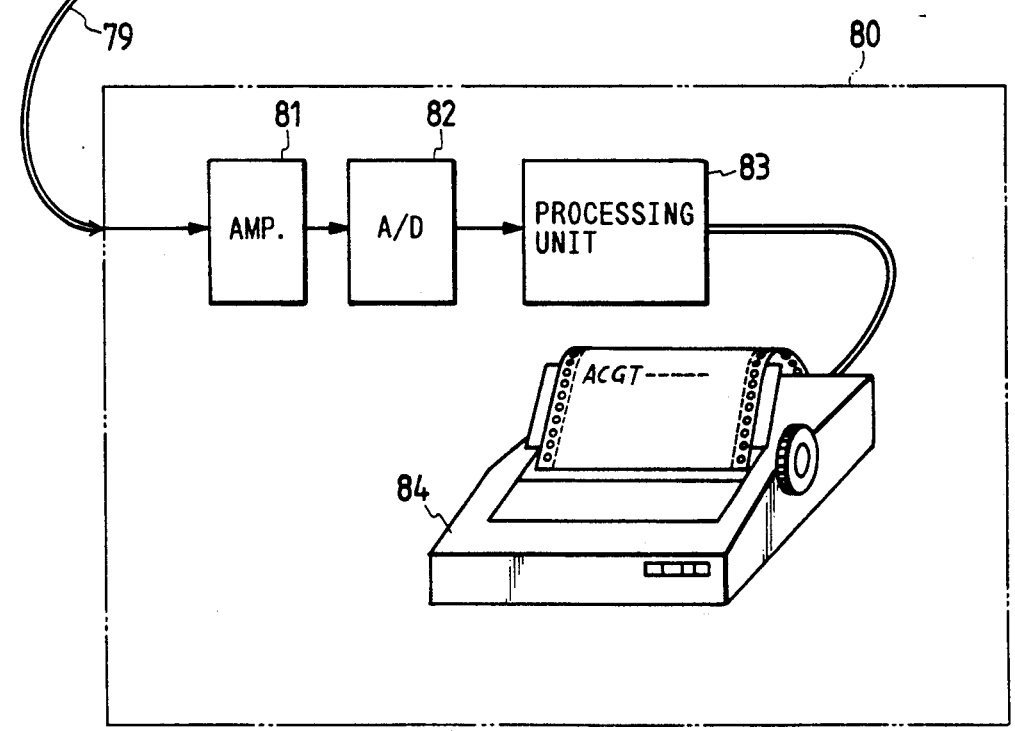

METHOD FOR TRANSCRIPTION OF A DNA SEQUENCE

This application is a continuation of application Ser. No. 07/287,113 filed Dec. 21, 1988 abandoned.

BACKGROUND OF THE INVENTION

The present invention relates to a method for transcription of a DNA sequence and, more particularly, to a method for transcription of the DNA sequence suitable for obtaining information of crude data detected as it is by a DNA sequencing apparatus using the fluorescent method. The present invention further relates to an apparatus for transcription of the DNA sequence adapted to acquire and record crude data of the DNA sequence detected by the DNA sequencing apparatus as it is.

The DNA sequencing apparatus using the fluorescent method has the advantage that a dangerous and expensive radioactive isotope is not required any more.

DNA sequencing on the basis of the fluorescent method is generally executed by electrophoresis using DNA fragments which are labelled with a fluorescent substance. The DNA fragments may be prepared by breaking down a DNA sequence sought to be subjected to sequence determination with restriction reagents in such a manner that bands of bases of various lengths are provided at terminals each with a specific one of four bases selected from a group of adenine (A), cytosine (C), guanine (G) and thymine (T) while controlling reactivities of chemical reactions specific to sites of base linkages. These fragments may be isolated by electrophoresis in accordance with lengths of bands of bases so that sequences of bases in the bands of bases can be determined from a distribution of intensities of fluorescence generated from the fluorescent substance labelled on each of the DNA fragments upon excitation.

An example of a distribution of DNA fragments after electrophoresis is shown in FIG. 9. As distances of electrophoresis vary with lengths of DNA fragments, it is to be noted that DNA fragments of identical molecular weights are gathered as time lapses, thus forming bands 91 corresponding to molecular weights and giving a distribution pattern of DNA as a whole as shown in FIG. 9. The bands in lanes 92, 93, 94 and 95 of respective bases, A, C, G, and T, are not located horizontally in a row because distances of electrophoresis vary from the other lanes due to a difference in molecular weights from the next band by more than one base.

A distribution pattern of a DNA fragments labelled with fluorescent substances may be produced by exposing a gel to laser beams or the like and detecting fluorescence generated upon reaction by a photoelectric converting element, while a distribution pattern of DNA fragments labelled with a radioactive substance may be irradiated on an X-ray film.

An electrophoresis apparatus adapted to detect a DNA sequence using the fluorescent detection method of the above type is described, for example, in Japanese Patent Publication (laid-open) No. 62,843/1986.

An electrophoresis apparatus is described in conjunction with FIG. 7 in which an electrophoresis apparatus 70 using the fluorescent method comprises an optical source 71 for exciting fluorescence, an optical fiber 72 for leading a light from the optical source 71, an electrophoresis unit 73 for carrying out electrophoresis, an upper electrode 74a and a lower electrode 74b for applying voltages to the electrophoresis unit 73, an electric source unit 75 for applying voltages to the electrodes, a lens system 76 for receiving fluorescence, an optical amplifier 77 for amplifying an optical signal, a one-dimensional optical sensor 78 for converting an image optically amplified into an electric signal, and a signal line 79 for supplying the electric signal from the optical sensor 78. Electric signals of a distribution pattern of a DNA fragment detected by the electrophoresis apparatus 70 are fed from the signal line 79 to a sequencing apparatus 80 in which the distribution pattern is sequenced and the resultant data is given. The sequencing apparatus 80 comprises an amplifier 81 for amplifying the electric signal fed from the signal line 79 in response to the electric signals of the distribution pattern of the DNA fragment detected by the electrophoresis apparatus 70, an analog-to-digital converting circuit 82 for converting an electric signal from analog to digital signals, a processing unit 83 for determining a sequence of bases from a digitized signal line, and an output unit 84 for outputting a signal line of the resultant base sequence.

Operation of the electrophoresis apparatus having the above structure will be described in conjunction with FIGS. 7, 8A, and 8B.

FIGS. 8A and 8B are a front view and a longitudinally cross-sectional view of the electrophoresis unit 73, respectively, which is shown to be constituted by a pair of glass plates 73b arranged so as to interpose a gel 73a, such as polyacrylamide, between both plates. A sample of DNA fragments is fed from an upper portion of the gel 73a of the electrophoresis unit 73 and the electrophoresis is executed by applying voltages from the upper and lower electrodes. A light, for example a laser beam, from the optical source 71 is radiated at an optical path 85 from the lower left-hand side in the drawing to the gel 73a of the electrophoresis unit 73 through the optical fiber 72. A fluorescent body of the DNA fragment in the gel 73a on the optical path 75 is excited to generate fluorescence 86.

The fluorescence 86 generated from the optical path 85 in the electrophoresis unit 73 is gathered and led to the optical amplifier 77 where an intensity of the light is amplified several thousand times to several tens of thousands of times. The amplified light is led to the one-dimensional optical sensor 78 where it is converted into electric signals. The one-dimensional optical sensor 78 is an optical sensor which is arranged in one-dimension so as to provide an image along the optical path 85. Electric signals as analog signals provided by the one-dimensional optical sensor 78 are then amplified by the amplifier 81 and digitized in the analog-to-digital (A/D) converting circuit 82. The digitized signals are fed to the processing unit 83 where a variation in fluorescent intensities at a virtually middle position of each of the lanes 92, 93, 94 and 95 on the optical path 85 is measured so as to judge whether a band is present or not, thus determining a sequence of bases consisting of A, C, G, and T. A sequence of the bases determined is converted into symbols such as letter codes or the like and printed out by a printer 84.

As has been described hereinabove, the DNA sequencing on the basis of the fluorescent method involves labelling DNA fragments with fluorescent substances, transferring a gel containing the labelled DNA fragments between a light emitting element of a laser and a photoelectric transfer element after electrophoresis, detecting fluorescence generated upon reaction with the laser beam or the like from the gel by the optoelectric transfer element, processing the detected data by means of the analog-to-digital conversion or other techniques to execute digital processing, and outputting only particular data corresponding to each base as a DNA sequence data with the printer or the like as letter data.

It is noted, however, that a conventional DNA sequencing apparatus for executing the DNA sequencing on the basis of the fluorescent method pays no great attention to the fact that a crude data of DNA sequences appearing on the gel as a fluorescent image can be left as an exhibit for evidence. It is further designed so as to digitize data detected by a photoelectric transfer element and output only particular data so that it suffers from the disadvantages that confirmation is impossible even if there is an error the processed results, the results may be falsified readily, and the competency of the results as scientific evidence is low. Further, prior art DNA sequencing apparatuses are made larger due to digital conversion of the data, digital analysis and the like and thus are rendered expensive.

SUMMARY OF THE INVENTION

The present invention has the object to provide a method for transcription of a DNA sequence adapted to retain information for digital analysis and the like on a recording medium as an intact image by transcribing the crude data of a DNA sequence obtainable by exposure of a gel to light and to provide information analyzable directly from transcribed information by manual operation without using an expensive DNA sequencing apparatus.

The present invention has another object to provide an apparatus for transcription of the DNA sequence and for executing the method for transcription of the DNA sequence.

In order to achieve the objects of the present invention, the DNA sequence transcribing method involves labelling DNA fragments with a fluorescent substance, transferring an electroptical transfer means and a photosensitive film relatively by following a movement of the gel containing the DNA fragments after electrophoresis, inputting to an electro-optical transfer means an output signal of the photoelectric transfer element, detecting fluorescence generated from the gel upon radiation of excited light such as a laser beam or the like, and recording a distribution pattern of the DNA fragments on the photosensitive film.

This allows the fluorescent image on the gel containing the DNA fragments labelled with the fluorescent substance after being subjected to electrophoresis to be recorded as a concentration distribution of the distribution pattern image on a recording medium intact as analog data without being processed by means of digital signal processing or the like, thus providing an image of substantially the same type as prepared by exposing a film to a gel labelled with a radioactive isotope. Accordingly, if the recording medium is paper, film or the like, crude data can be stored as evidence and information for digital analysis or the like, and this film or the like may be used for sequencing with a DNA sequencing analyzer or the like, thus requiring no excessive apparatus such as a digital analyzer or the like.

Furthermore, in order to achieve the above objects of the present invention, the DNA sequence transcribing apparatus comprises the electrophoresis unit in which electrophoresis is executed using the DNA fragments labelled with the fluorescent substance, a light radiating unit for radiating an excited light to the electrophoresis unit so as to cross a direction of electrophoresis, a light receiving unit in which light receiving elements are arranged in a direction perpendicular to the direction of electrophoresis so as to receive fluorescence generated by the excited light radiated by the light radiating unit, and a recording unit for recording scans of a distribution of intensities of the fluorescence received by the light receiving unit.

The recording unit is designed such that the distribution of intensities of the fluorescence received by the light receiving unit is acquired at an interval of a predetermined time and the intensity distribution of fluorescence is recorded on a recording medium after re-building it by scanning two-dimensionally a direction of arrangement of the light receiving elements of the light receiving unit as a first axis and a direction of a time lapse as a second axis.

The DNA sequence transcribing apparatus having the above structure is designed so as to successively store a variation of fluorescence passing through a position of a detector by setting a direction of scanning by the detector with respect to the gel in such a state that electrophoresis is executed in the gel to which the DNA fragments labelled with the fluorescent substance are fed. The stored data is recorded on a photosensitive film or the like on an axis other than the axis of scanning in accordance with a lapse of time.

This permits an image formed in a time lapse during electrophoresis by fluorescence on the gel containing the DNA fragments labelled with the fluorescent substance to be recorded intact as a concentration distribution image of analog data or digital data of a dot image, thus providing an image of substantially the same type as prepared by exposing an X-ray film to the gel labelled with a radioactive isotope.

Accordingly, if the recording medium is paper, film or the like, crude data can be stored as evidence and information for digital analysis and the like. Using this film or the like, a conventional apparatus may be used for sequencing and therefore an expensive analyzer apparatus is not required any more.

BRIEF DESCRIPTION OF THE DRAWINGS

Other objects and features of the present invention will become apparent by way of description on the following preferred embodiments in conjunction with the drawings, in which:

FIG. 7 is a view showing a structure of an essential portion of the DNA sequencing apparatus using the fluorescent method.

DESCRIPTION OF THE PREFERRED EMBODIMENTS

Figure 1:
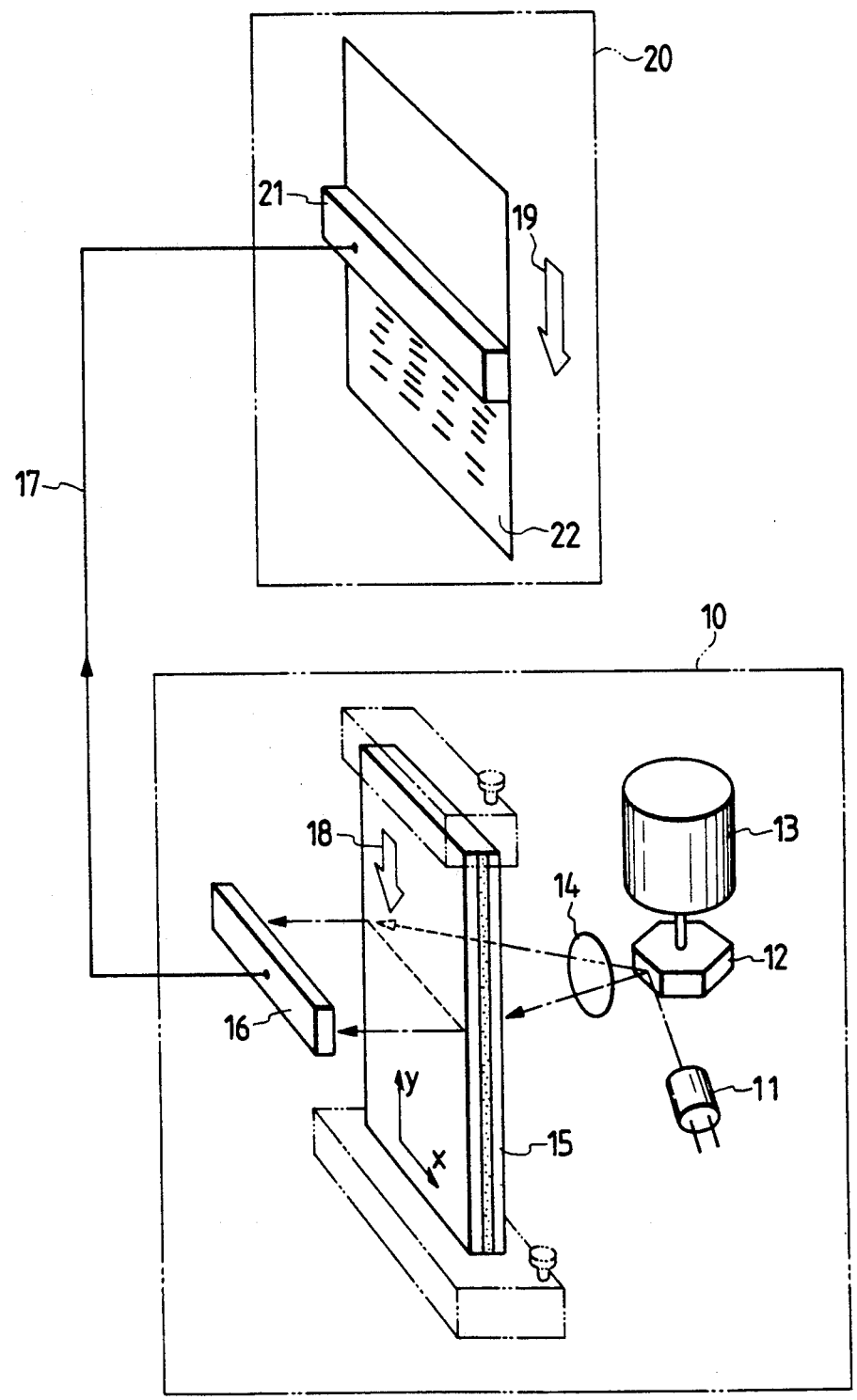
FIG. 1 is an explanation drawing for explaining the principle of the DNA sequence transcribing method as a preferred example according to the present invention.

Referring to FIG. 1, there will be described the principle of the DNA sequence transcribing method as a preferred embodiment according to the present invention. As shown in FIG. 1, the DNA sequence transcribing method involves recording signals from the electrophoresis unit 10 by the recording unit 20 in accordance with electrophoresis, the electrophoresis unit 10 comprising a semiconductor laser 11 as a light source, a rotary polygon mirror 12 for reflecting laser beams generated by the semiconductor laser 11 and scanning the electrophoresis subunit 15, a motor 13 for rotating the polygon mirror 12, a lens 14 for focusing the laser beams, an electrophoresis subunit 15 containing a gel obtained by subjecting DNA fragments to electrophoresis, and an optoelectric transfer element 16 for receiving fluorescence generated by the gel in the electrophoresis subunit 15. The recording unit 20 comprises an electroptical transfer element 21, a photosensitive film 22 for transcription, and a film winding mechanism (not shown) and is designed such that signals from the electrophoresis unit 10 are transferred relatively through the electroptical transfer element 21 to the photosensitive film 22 in accordance with electrophoresis and that signals of a distribution pattern of the DNA fragments are recorded, thus transcribing DNA fragments.

More specifically, the DNA fragments labelled with a fluorescent substance are fed to the electrophoresis subunit 15 and transferred in the gel at a constant velocity in a direction given by the arrow 18 (a direction of electrophoresis) by means of electrophoresis. The laser beams generated by the semiconductor laser 11 are reflected by the rotary polygon mirror 12 and the reflected laser beams are focused by the lens 14 for exposure to the gel 15 of the DNA fragments. As the polygon mirror 12 rotates, the laser beams are radiated in such a manner as scanning the electrophoresis subunit 15 with the gel containing the DNA fragments in an x-direction, namely, in a direction perpendicular to the direction of electrophoresis. The rotary polygon mirror 12 is rotated by the motor 13 such that a speed of the laser beams scanning the electrophoresis subunit 15 (namely, a main scan speed) is much faster than a speed of the DNA fragments migrating in the gel in a y-direction (namely, a sub-scan speed).

Exposure to the laser beams allows the DNA fragments in the gel of the electrophoresis subunit 15 to generate an amount of fluorescence proportional to an amount of the fluorescent substance contained at a portion to which the laser beams are exposed. The photoelectric transfer element 16 is one-dimensionally arranged at a position interposing the electrophoresis subunit 15 and facing the rotary polygon mirror 12 and in a length corresponding to a width of the ectrophoresis subunit 15. This arrangement permits an image of fluorescence of the DNA fragment in the gel generated by excitation of the laser beams upon reaction to be detected at every scanning by the photoelectric transfer element 16 as the electrophoresis subunit 15 is scanned by the reflected laser beams from the rotary polygon mirror 12 in the x-direction, thus converting into electric signals 17. The scanning in the x-direction is repeated successively in the direction 18 of electrophoresis, namely, in the y-direction.

The photosensitive film 22 on the side of the recording unit 20 is arranged so as to be likewise transferred in the y-direction, viz., in the direction of electrophoresis, by the film winding mechanism (not shown) in accompany with a transferal of the electrophoresis subunit 15 in a direction as given by the arrow 19. In the recording unit 20, the electroptical transfer element 21 is disposed one-dimensionally nearby the film 22 in a direction perpendicular to a direction of movement of the film 22, namely, in the x-direction, and the electroptical transfer element 21 and the optoelectric converting element 16 are connected so as to allow their bit positions to correspond to each other. This arrangement permits an input of the electric signal 17 detected by the photoelectric transfer element 16 in the electroptical transfer element 21 in a bit correspondence at every scan as the electrophoresis subunit 15 is scanned by the laser beams, thus converting to light and exposing the film 22 in the x-direction. This operation is repeated successively in the y-direction of the film 22 in synchronization with transferal of the gel in the electrophoresis subunit 15 in the y-direction. A fluorescent image of the electrophoresis subunit 15, namely, a DNA sequence image, is thus transcribed on the film 22 and remains intact.

In the above embodiment, a photosensitive recording system consisting of the electroptical transfer element 21 and the photosensitive film 22 is used as the method for transcribing the electric signals that are detected. It is to be noted herein that there may be obviously employed a thermal recording system using an exothermic head and thermal paper, an electrical discharge recording system using electrical discharge, a static recording system using static electricity, and the like. As a recording medium for transcription, a magnetic recording medium and the like may also be employed.

In the above embodiment, too, there are used sensors arranged one-dimensionally for detection and transcription of the fluorescent image of the electrophoresis subunit. It is also obvious to use a sensor of a pixel unit and a sensor system arranged in two-dimensionally.

As have been described hereinabove, the DNA sequence transcribing method and apparatus according to the present invention enables a crude fluorescent image of the gel containing DNA fragments to be transcribed as an intact image of the DNA sequencing on the basis of the fluorescent method so that it may be used as evidence and information on the DNA sequencing. This permits an analaysis of a DNA sequence directly from transcribed results even without an expensive and laborious analyzer.

Figure 2:
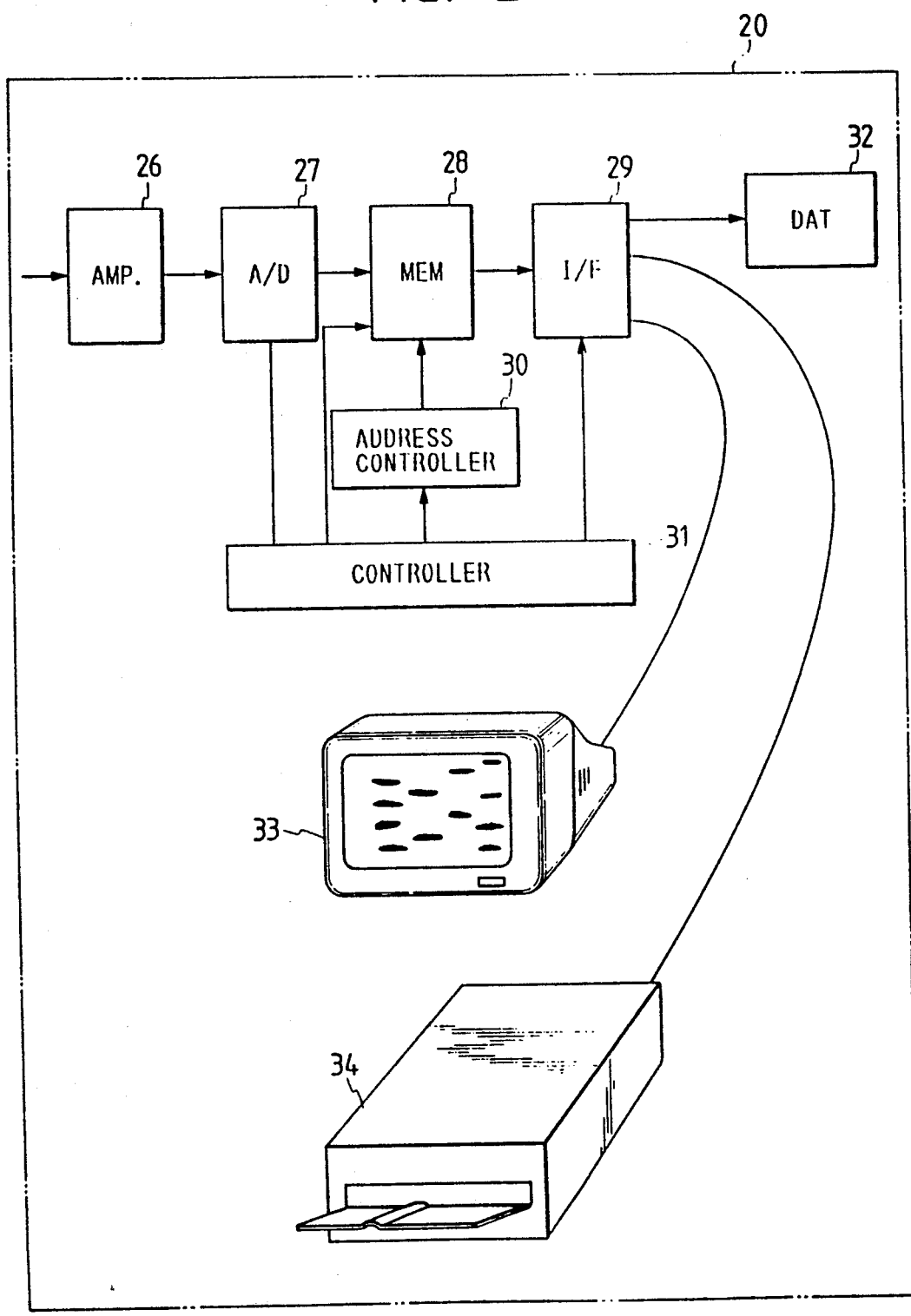
FIG. 2 is a view showing a structure of an essential portion of the DNA sequence transcribing apparatus as a preferred example according to the present invention.

FIG. 2 is a view illustrating a structure of the essential portion of the DNA sequence transcribing apparatus as another example of the present invention. In FIG. 2, only the recording unit 20 is shown as the essential portion of the DNA sequence transcribing apparatus. As a device for feeding electric signals of a distribution pattern of a DNA fragment to the recording unit 20, there may be used the electrophoresis unit 10 as shown in FIG. 1 or an electrophoresis unit 70 as shown in FIG. 7, for example.

As shown in FIG. 2, the DNA sequence transcribing apparatus as another example contains a recording unit which comprises an analog-to-digital (A/D) converting circuit 27 for digitizing electric signals from an amplifier 26, a memory 28 for storing data obtained by the analog-to-digital (A/D) converting circuit 27, an interface unit 29 for connecting the memory 28 to an output device, an address control circuit (address controller) 30 for allocating an address for writing data on the memory 28, a control unit (controller) 31 for controlling the system, a display 33 for displaying an image, and a film printer 34 for storing data as films.

The electric signals from the electrophoresis unit are amplified by the amplifier 26 to an appropriate level and applied to the analog-to-digital converting circuit 27. In this embodiment, a quantization number is 8 bits, for example. A digitizing timing is given by the control unit 31, and a timing signal is also given to the address control circuit 30 synchronizing an address generated from the address control circuit 30 with the writing of data. Image data is stored in the memory 28 in a time series.

Figure 3:
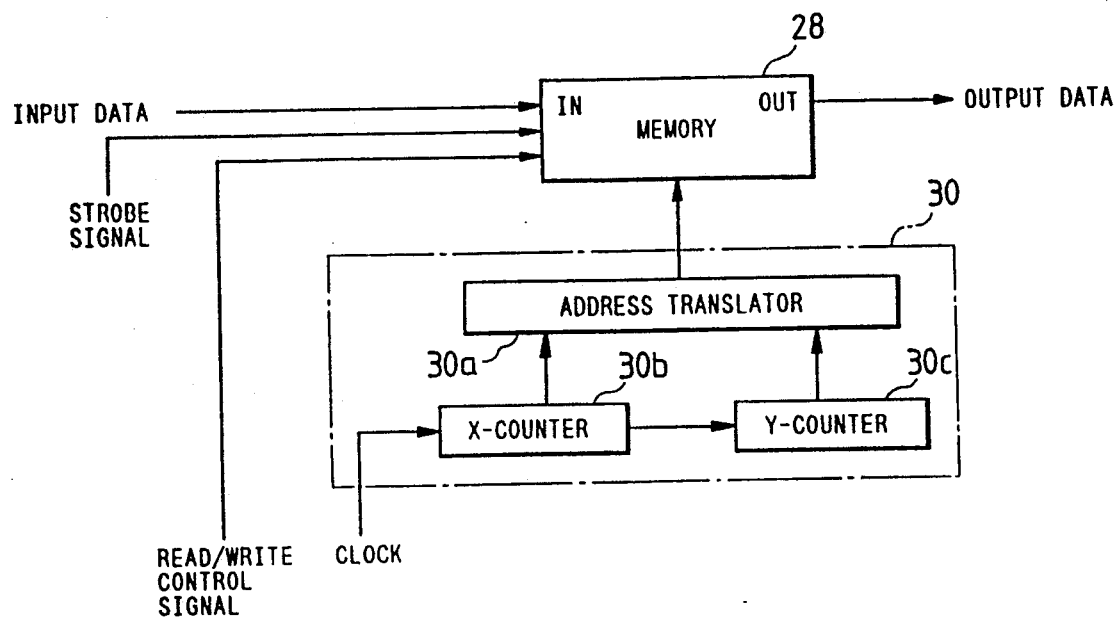
FIG. 3 is a block diagram showing a structure of a memory and address control circuit of the DNA sequence transcribing apparatus of FIG. 2.

Essential structures of the memory 28 and the address control circuit 30 are shown in FIG. 3. As shown in FIG. 3, the address control circuit 30 comprises an address translator 30a, an X-counter 30b and a Y-counter 30c. The X-counter 30b is a counter for repeatedly counting, for example, 2376 counts from "0" to "2375" and is designed so as to generate a carry signal at the count "2375". The carry signal is then added to the Y-counter 30c which in turn is increased by 1 increment. The address translator 30a is to translate addresses for an efficient use of the memory 28. Generally, a capacity of the memory 28 is the sum given by raising 2 to N-th power if a number of address input is "N". In this case, addresses range from "0" to "$2^N-1$". In this embodiment, a data number in the x-direction is 2376 so that at least 12 bits of addresses ($2^{11}=2048<2376<2^{12}=4096$). Accordingly, if a memory is addressed simply by allocating output of the Y-counter 30c at a high order address and allocating output of the X-counter 30b at a low order address, addresses ranging from "2376" to "4095" are not used for each Y address value. This causes poor efficiency in use of the memory. In order to avoid this inefficiency, the address translator 30a is designed so as to execute translation as follows:

Memory address $= Y \times 2376 + X$ (1)

Computation of addresses by calculating the above formula requires basically an adder and a multiplying calculator.

Accordingly, in this embodiment, the first term in the right-hand side of the formula (1) is multiplied in advance and written in ROM (read only memory). RAM (random access memory) or the like having addresses more than the maximum value of Y. Thus the multiplication becomes merely a ROM access, simplifying a circuit and rendering it cheaper and faster. This also can readily deal with an alteration in a number of pixels in the x-direction. The address control circuit 30 may be constituted, for example, by an adder that adds such ROM and the X-counter.

Figure 4:
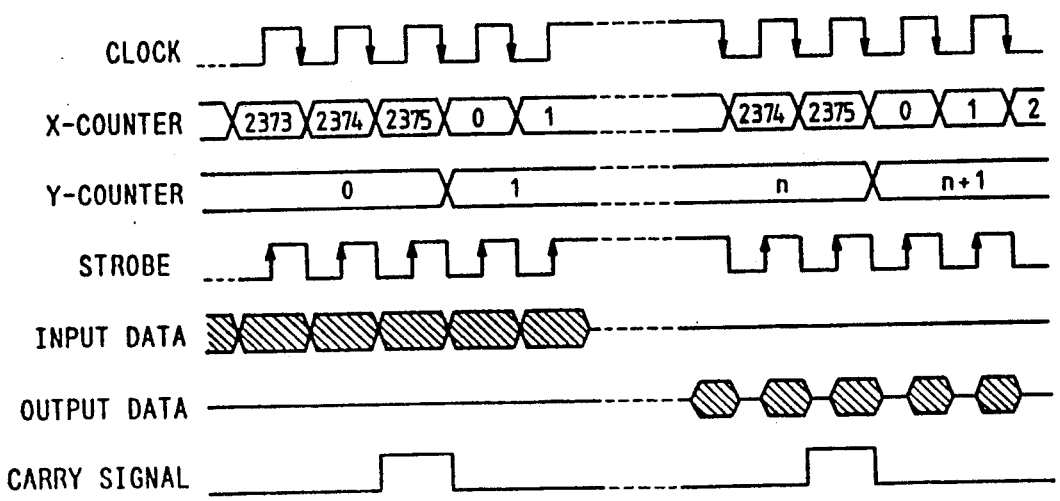
FIG. 4 is a timing chart for explaining operation of recording in a memory shown in FIG. 3.

These operations will be described with reference to the timing chart shown in FIG. 4. First, the case of writing output from the analog-to-digital converter 27 in the memory 28 will be described. Referring to the left-hand portion of FIG. 4, the X-counter 30b is incremented at the rise of clock pulses from the control unit 31. As the count value reaches 2375 at the X-counter, the carry signal is given as shown in FIG. 4, incrementing the Y-counter 30c by one. A data, namely, an oblique portion, from the analog-to-digital converter 27 gives output to an input data line in synchronization with the rise of the clock pulses, and the memory 28 is written at the rise of a strobe signal that is stable in address and data.

Figure 5:
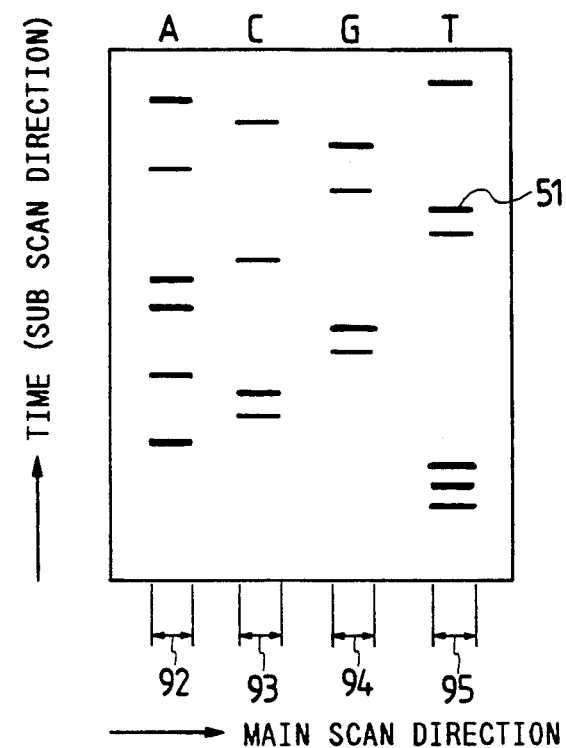
FIGS. 5, 6A and 6B are each a view showing an example of a distribution pattern of a DNA fragment subjected to electrophoresis and a scan direction for recording.
Figure 6A:
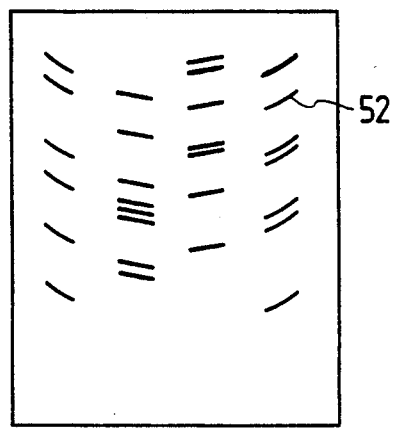
Figure 6B:
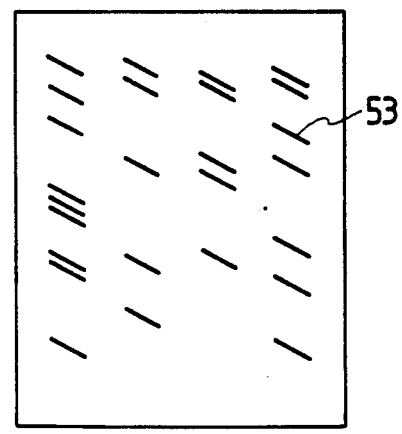
Figure 8A:
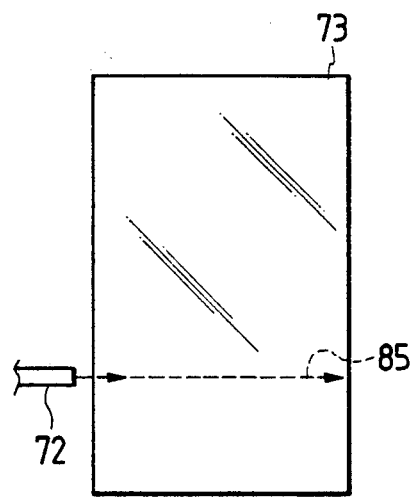
FIGS. 8A, 8B and 9 each is a view for explaining the principle of the DNA sequencing apparatus using the fluorescent method.
Figure 8B:
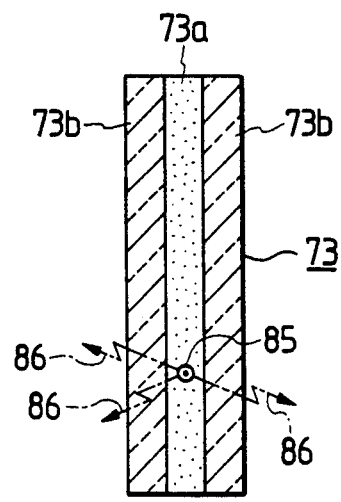
Figure 9:
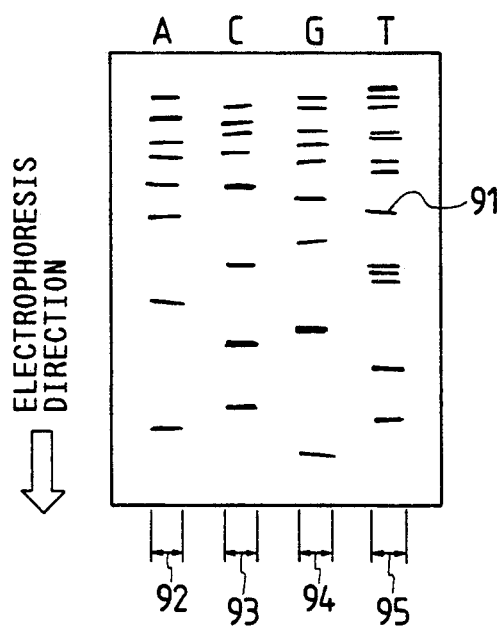

Secondly, referring to the right-hand portion of FIG. 4, there will be described the case of reading a data from the memory for outputting the data or the like. As shown in FIG. 4, a timing of this reading operation generates a reading address by adding clock pulses in the same manner as in the writing operation as above. As a strobe signal reaches a high level, a data is output during a period when the strobe signal is at a high level. This output is then fed to the interface unit 29 (FIG. 2) which is provided with a function of converting digital to analog signals in addition to the function of outputting a digital data intact from the memory. That function permits output of the data to be given intact on the basis of instruction from the control unit 31 to a DAT (digital/audio tape recorder) 32 or to be given to the display 33 as a video signal that is converted into an analog signal. Such output may be stored by an optical film printer 34 as required. As output results, for example, electrophoresis patterns of DNA are given as shown in FIGS. 5, 6A and 6B. In these image patterns, the horizontal axis is the main scan direction, while the vertical axis is a direction in which time lapses. For example, in the case of a signal from the electrophoresis unit 70 as shown in FIG. 7, it is a direction in which the one-dimensional sensor is arranged along the optical path 85. In this case, an arrangement for bands 51 corresponding to positions of DNA fragments is different from those illustrated in FIG. 9, in which minimum pitches of the vertical axis are at virtually equal distances as a whole. This is because FIG. 5 is a fluorescence distribution at the time when a DNA fragment passes through a position of the optical path 85 while FIG. 9 shows an image of a whole electrophoresis surface in the process of electrophoresis.

As shown in FIGS. 6A and 6B, a distribution pattern of DNA fragments by electrophoresis may be curved (called "smiling") like bands 52 or inclined like bands 53. This may occur because of various reasons such as a variation in a temperature distribution generated during electrophoresis or in a gel state. Even in such a state, electric signals of a distribution pattern of DNA patterns subjected to electrophoresis are recorded, thus ensuring an assumption of band positions between each of lanes.

In the embodiment shown in FIG. 2, the memory 28 is provided as have been described with respect to the basic principle of the DNA sequence transcribing method as shown in FIG. 1. It is to be noted, however, that such a memory can be cancelled by synchronizing operation of the film printer 34, the display 33, the digital/audio tape recorder 32 or the like with operation of the analog-to-digital converter 27. Although output of the image signal is given after it is once converted to digital signals in this embodiment, too, it is possible to add analog signals directly to an electroptical transfer element, thus printing on a film.

As will be apparent from the foregoing description, the above embodiments are directed to the case where a fluorescent image on the gel containing DNA fragments labelled with a fluorescent substance and obtained during electrophoresis is recorded as an analog data or a digital data on a recording medium as a concentration distribution of the image as it is intact, thus permitting an image of substantially the same type as prepared by X-ray films exposed to a gel labelled with a radioactive isotope.

Accordingly, if the recording medium is paper or film, crude data is stored as evidence and information for digital analysis or the like. Sequencing with a machine such as a DNA sequence analyzer or the like using this film or the like does not require any more such expensive equipment as a digital analyzer or the like.

Sequencing can be ensured even if smiling or other irregularities would occur during electrophoresis.

Although the present invention has been specifically described by way of examples, it should be understood that the present invention is not restricted to those embodiments and is interpreted as encompassing various modifications within its scope without departing from the spirit of the invention.

As have been described hereinabove, the present invention permits a crude fluorescent image of a gel containing DNA fragments to be recorded intact as an image in the DNA sequencing on the basis of the fluorescent method, thus employing such an image as evidence and information for DNA sequencing. Furthermore, the recording of the resultant pattern enables an analysis of a DNA sequence directly from the recorded results even without using an expensive and laborious analyzer.

What is claimed is:

1. A method for transcription of a DNA sequence, comprising the steps of:

labeling DNA fragments with a fluorescent substance;

subjecting the labeled DNA fragments to gel electrophoresis to cause migration of the fragments in the gel in a first direction;

inducing fluorescence of the labeled DNA fragments by excitation with an optical source by linearly scanning the gel along a path extending in a second direction perpendicular to said first direction;

detecting the fluorescence generated from the excitation with a photoelectric device arranged in said second direction to produce a signal that varies in intensity along the scanning path in accordance with the fluorescence and outputting the signal;

receiving and recording said output signal with an electro-optical transfer device on a photosensitive film as an image of the gel containing the labeled DNA fragments; and moving one of said electro-optical transfer device and said photosensitive film relative to the other at a rate corresponding to a rate of the migration of the DNA fragments within the gel to record a series of said output signals separated from one another by said moving.

* * * * *